United States Patent [19]

Blakemore

[11] 4,163,384
[45] Aug. 7, 1979

[54] PIEZOELECTRIC MOISTURE ANALYZERS

[75] Inventor: Colin B. Blakemore, Wilmington, Del.

[73] Assignee: E. I. Du Pont de Nemours and Company, Wilmington, Del.

[21] Appl. No.: 896,449

[22] Filed: Apr. 14, 1978

[51] Int. Cl.² ............................................. G01N 31/00
[52] U.S. Cl. ....................................................... 73/29
[58] Field of Search ............................. 73/29, 23, 1 G

[56] References Cited

U.S. PATENT DOCUMENTS

| | | | |
|---|---|---|---|
| 3,260,104 | 7/1966 | King | 73/23 |
| 3,266,291 | 8/1966 | King | 73/23 |
| 3,427,864 | 2/1969 | King | 73/29 |
| 3,677,066 | 7/1972 | King et al. | 73/23 |

*Primary Examiner*—Anthony V. Ciarlante

[57] ABSTRACT

The sensitivity to moisture of polystyrene sulfonate coatings on piezoelectric crystals in moisture detectors is unstable in the presence of acid gases. The sensitivity of these coated crystals can be stabilized by contacting the polymer with an acid gas.

7 Claims, No Drawings

PIEZOELECTRIC MOISTURE ANALYZERS

BACKGROUND OF THE INVENTION

This invention relates to improved piezoelectric moisture analyzers. The analyzers of this invention are particularly useful for moisture measurements in gas streams which also contain acid gases.

Piezoelectric moisture analyzers are well-known instruments. Their construction and use are described in a series of patents to W. H. King, Jr., beginning with U.S. Pat. No. 3,164,004 and a patent to H. M. Crawford, U.S. Pat. No. 3,327,519. In these devices a piezoelectric crystal such as quartz is coated with a substance which is responsive to moisture. Useful materials include polymers such as the sulfonic acid and sulfonate salts of polystyrene which reversibly form hydrates when exposed to moisture. The change in the mass of the coating on the crystal causes a measurable change in the frequency of oscillation of the crystal in an electrical oscillation circuit. This change, which can be electrically detected, provides a measure of the moisture content of the environment in which the coated crystal is placed.

It has been recognized that moisture detectors of the type described above suffer a loss of sensitivity when the gas stream to be analyzed contains an acid gas in addition to moisture. That is, when an acid gas is present in the gas stream, the amount of moisture which can be detected decreases, and the change in the frequency response of the coated crystal to a constant moisture concentration decreases. This loss of sensitivity has been observed whether the polymer coating on the crystal is in the form of a sulfonic acid or a sulfonic acid salt. The loss in sensitivity due to the presence of acids in gases has limited the usefulness and accuracy of piezoelectric moisture analyzers in industrial gas streams containing acids. One example of this problem is in the measurement of moisture in natural gas which frequently also contains $H_2S$.

It has now been found that the piezoelectric moisture analyzers of the prior art can be improved to be more stable in gas streams in which an acid gas is present. The coated crystals are stabilized by contacting them with an acid gas for a sufficient period of time to reduce the sensitivity to moisture of the coated crystal to a range in which the stability is no longer affected by the acid gas. Typically, the frequency response of the crystal in the region of stable sensitivity is about 30 to 50 percent lower than the original level of the coated crystal. The acid gas used to stabilize the coated crystal need not be the same as the acid gas found in the gas stream in which the moisture is to be measured. However, it should be recognized that the gas used to stabilize the coated crystal must be selected so that the coated crystal after stabilization will not react with the acid gas of the gas stream to be measured. If such a reaction were to occur, there would be a further alteration of the sensitivity of the coated crystal. Thus, it is preferred that the gas chosen to stabilize the crystal is the same as the gas that is found in the gas stream which will be monitored by the instrument. The stabilization of the coated crystals occurs faster if the acid gas used is moist with water vapor or, is saturated with water vapor. The preferred acid gases for the stabilization step are $H_2S$, HCl, $NO_2$ and $SO_2$ with $H_2S$ being the most preferred.

The preferred water sensitive polymer for coating the piezoelectric crystals in this invention is sodium polystyrene sulfonate. Of course, if the polymer coating used in the analyzer is a sulfonic acid salt prior to the stabilization step, the polymer can be converted to a sulfonic acid. If the inorganic salt formed as a result of this reaction is not volatile, it will remain on the surface of the polymer.

The loss of sensitivity appears irreversible and must be compensated for in the calibration of the moisture detector. However, the stable sensitivity, even though it is lower, permits accurate measurement of moisture in gas. Such accurate measurements are not possible so long as the sensitivity of the instrument is unstable.

In a preferred method for preconditioning the coated piezoelectric crystal, the coated crystal is exposed to a high concentration of the acid gas or the pure gas containing moisture. In the case of $H_2S$, preconditioning a crystal coated with sodium polystyrene sulfonate by contacting it with pure $H_2S$ saturated with water for about 36 hours at room temperature reduces the sensitivity of the coated crystal to moisture to a stable sensitivity level about 50% less than the original sensitivity. The same procedure can be used with acid gases such as HCl or moist $SO_2$ or $NO_2$.

Since the moisture analyzers of this invention are particularly useful in acid environments, all of the components of the analyzer which contact the gas streams must be acid resistant. In the most preferred embodiment, the electrode layer on the crystal is gold and the metal used in the conductive adhesive which binds the crystal to its mounting posts is gold.

EXAMPLE I

A moisture analyzer was equipped with a piezoelectric crystal having gold electrode layers which were partially coated with sodium polystyrene sulfonate. A calibration curve was developed by measuring the natural frequency of oscillation of the crystal in the analyzer's oscillation circuit in response to various known moisture concentrations. The crystal was then exposed to a gas stream containing 30% $H_2S$ and 95 parts per million by volume (ppm) of water vapor. Although the moisture content of the gas stream was held constant, the moisture content indicated by the calibration curve fell rapidly so that the indicated moisture content had fallen to approximately 83.5 ppm after 6.33 hours exposure and approximately 78 ppm after 13.75 hours. After 21.25 hours exposure, the indicated moisture concentration fell to about 73 ppm, a decline of about 23%. However, over the next 50 hours of exposure, the indicated moisture concentration remained substantially stable, falling to 69.8 ppm. Thus, after the initial period of sharp decline of indicated moisture levels, a new calibration curve could be developed to accurately indicate moisture concentrations.

EXAMPLE II

The experiment of Example I was repeated using a piezoelectric crystal coated with polystyrene sulfonic acid. The coated crystal was exposed to a gas stream containing 30% $H_2S$ and 280 ppm water. The indicated moisture level fell rapidly from 280 ppm at 0 hour of exposure to 71 ppm after 42.24 hours of exposure, after which a new calibration curve could be developed to yield accurate moisture data.

I claim:

1. In a moisture analyzer for measuring the moisture content of a gas stream which contains a first acid gas comprising a piezoelectric crystal coated with a polymer selected from the group consisting of polystyrene sulfonic acid and salts of polystyrene sulfonic acid, the improvement wherein the sensitivity of the coated crystal to water in the presence of acid is stabilized by exposure of the coated crystal to a second acid gas which can be the same or different than the first acid gas for a period of time sufficient to produce stable sensitivity of the coated crystal to moisture in the presence of the first acid gas.

2. The analyzer of claim 1 wherein the second acid gas used to stabilized the coated crystal is moist, is the same as the first acid gas, and is selected from the group consisting of $H_2S$, $HCl$, $NO_2$ and $SO_2$.

3. The analyzer of claim 1 wherein the piezoelectric crystals have a gold electrode layer.

4. The analyzer of claim 2 or 3 wherein the polymer is sodium polystyrene sulfonate and the acid gas is $H_2S$.

5. In a method for measuring the moisture content of a gas stream containing a first acid gas comprising placing the gas stream in contact with a piezoelectric crystal coated with a polymer selected from the group consisting of polystyrene sulfonic acid and polystyrene sulfonic acid salts and noting the change of the natural frequency of vibration of the crystal in an oscillator circuit in response to moisture in the gas stream, the improvement comprising stabilizing the coated crystal by contacting it with a second gas for a sufficient period of time to produce a stable sensitivity of the coated crystal to moisture in the presence of the first acid gas.

6. The method of claim 5 wherein the second acid gas used to stabilize the coated crystal is the same as the first acid gas, and is a moist gas selected from the group consisting of $H_2S$, $HCl$, $SO_2$ and $NO_2$.

7. The method of claim 6 wherein the acid gas is $H_2S$.

* * * * *